United States Patent
Ito et al.

(10) Patent No.: US 8,530,186 B2
(45) Date of Patent: Sep. 10, 2013

(54) METHOD FOR PRODUCING GLUCURONIC ACID BY GLUCURONIC ACID FERMENTATION

(75) Inventors: Tetsuya Ito, Tokyo (JP); Yuki Ario, Tokyo (JP); Eriko Kishino, Tokyo (JP); Koki Fujita, Tokyo (JP)

(73) Assignee: Ensuiko Sugar Refining Co., Ltd., Tokyo (JP)

( * ) Notice: Subject to any disclaimer, the term of this patent is extended or adjusted under 35 U.S.C. 154(b) by 876 days.

(21) Appl. No.: 12/598,456

(22) PCT Filed: Apr. 21, 2008

(86) PCT No.: PCT/JP2008/057706
§ 371 (c)(1),
(2), (4) Date: Nov. 2, 2009

(87) PCT Pub. No.: WO2008/139844
PCT Pub. Date: Nov. 20, 2008

(65) Prior Publication Data
US 2010/0075381 A1    Mar. 25, 2010

(30) Foreign Application Priority Data
May 8, 2007 (JP) ................................. 2007-123975

(51) Int. Cl.
*C12N 1/12* (2006.01)
*C12N 1/20* (2006.01)
*C12P 1/00* (2006.01)
*C12P 1/04* (2006.01)
*C12P 7/00* (2006.01)

(52) U.S. Cl.
USPC .......... 435/41; 435/132; 435/170; 435/252.1; 435/822

(58) Field of Classification Search
None
See application file for complete search history.

(56) References Cited

U.S. PATENT DOCUMENTS
5,434,061 A * 7/1995 Ishiguro et al. ............... 435/100

FOREIGN PATENT DOCUMENTS

| | | |
|---|---|---|
| EP | 1111065 A2 * | 6/2001 |
| JP | H5-68542 | 3/1993 |
| JP | H6-7157 | 1/1994 |
| JP | H07-076594 | 3/1995 |
| JP | H10-251263 | 9/1998 |
| JP | H11-147043 | 6/1999 |
| JP | 2003-159079 | 6/2003 |
| JP | 2006-314223 | 11/2006 |

OTHER PUBLICATIONS

Japanese Examined Patent Publication S43-5882, Mar. 4, 1968.
International Search Report received in PCT/JP2008-057706 mailed May 13, 2008.

* cited by examiner

*Primary Examiner* — Debbie K Ware
(74) *Attorney, Agent, or Firm* — Suzannah K. Sundby, Esq.; Smith, Gambrell & Russell, LLP

(57) ABSTRACT

The object of the present invention is to provide a microorganism having an excellent ability to specifically oxidize the hydroxymethyl group of glucose, and a method of producing glucuronic acid and/or glucuronolactone by using such a microorganism to directly oxidize glucose, and the invention is directed at a microorganism which produces glucuronic acid directly from glucose and a mutant strain which is capable of specifically oxidizing the hydroxymethyl group of glucose and in which a DNA nucleotide sequence corresponding to 16S rRNA has the nucleotide sequence of SEQ ID NO: 1 in the sequence listing, and the invention is also directed at a method of producing glucuronic acid and/or glucuronolactone by specifically oxidizing the hydroxymethyl group of glucose using the mutant strain, and this invention enables D-glucuronic acid and/or D-glucuronolactone to be produced and furnished easily and safely at a high yield and a low cost.

6 Claims, No Drawings

METHOD FOR PRODUCING GLUCURONIC ACID BY GLUCURONIC ACID FERMENTATION

TECHNICAL FIELD

The present invention relates to microorganisms which specifically oxidize the hydroxymethyl group of glucose, and to a method for producing glucuronic acid and/or glucuronolactone using such microorganisms. More specifically, the invention relates to novel mutant strains for glucuronic acid fermentation which have the ability to specifically oxidize the hydroxymethyl group of glucose and the ability to directly produce glucuronic acid from glucose at a high selectivity, and to a method for producing glucuronic acid and/or glucuronolactone by glucuronic acid fermentation using such mutual strains.

BACKGROUND ART

Gluconic acid, in which the aldehyde group of D-glucose has been oxidized, and glucuronic acid, in which the hydroxymethyl group of D-glucose has been oxidized, are known as typical oxides of D-glucose. Gluconic acid and the lactone thereof, which is gluconolactone, are formed by the oxidative fermentation (gluconic acid fermentation) of glucose by a microorganism. Microorganisms such as *Aspergillus niger* and *Penicillium chrysogenum* are used in the industrial production of these compounds.

Although various methods are known for producing glucuronic acid and the lactone form thereof, which is glucuronolactone, one method that has actually been industrialized is a process wherein a glucose derivative such as starch is selectively oxidized using a nitrogen oxide compound such as nitric acid and thereby converted to a carboxylic acid, following which the product of oxidization is hydrolyzed to give glucuronic acid and glucuronolactone (Patent Document 1). However, in this process, the by-product gases that form during the oxidation reaction are difficult to handle, resulting in a low yield of the target substance.

The prior art also includes a method for obtaining glucuronic acid and glucuronolactone in a high yield wherein trehalose oxide is prepared by oxidizing the hydroxymethyl group of trehalose, following which the trehalose oxide is hydrolyzed to form the desired glucuronic acid and glucuronolactone (Patent Document 2). However, although this method does provide a good yield of the target substance from the starting material, it requires a large amount of oxidation catalyst such as platinum oxide, vanadium oxide or palladium, in addition to which relatively extreme conditions are needed to hydrolyze trehalose oxide, all of which results in considerable production costs.

Another method that has been described involves using an oxidation catalyst resin to which has been adsorbed an amine oxide such as 6,6-tetramethylpiperidine-N-oxyl to oxidize a glucose derivative in the presence of a halogen-containing compound (Patent Document 3). Because nitrogen oxides such as nitric acid are not used in this method, glucuronic acid and glucuronolactone can be safely and efficiently obtained. However, the glucose derivatives preferred for use in this method are the high-cost compounds methyl-α-D-glucoside and isopropyl-(α, β)-D-glucoside. Hence, as with the above-described methods, this method also entails substantial production costs.

A relatively inexpensive glucuronic acid production process that has been described involves producing a sucrose carboxylic acid from sucrose by oxidative fermentation with a microorganism, then adding a microorganism having an invertase activity and hydrolyzing the sucrose carboxylic acid so as to obtain glucuronic acid and glucuronolactone (Patent Document 4). In this process, unlike conventional chemical synthesis processes, glucuronic acid and glucuronolactone may be obtained in high yields under mild conditions. However, the need to use two different microorganisms in the series of production steps making up this process complicates the operations.

To produce glucuronic acid directly from glucose as in gluconic acid fermentation, it is necessary to specifically oxidize the hydroxymethyl group of glucose. Enzymes that are known to oxidize the hydroxymethyl group of glucose include alcohol dehydrogenase (Patent Document 5) and alcohol/aldehyde dehydrogenase (Patent Document 6). *Pseudogluconobacter* sp. are known to be strains having these enzymes.

Illustrative examples of these strains include *Pseudogluconobacter saccharoketogenes* K591s (FERM BP-1130, IFO14464), *Pseudogluconobacter saccharoketogenes* 12-5 (FERM BP-1129, IFO14465), *Pseudogluconobacter saccharoketogenes* TH14-86 (FERM BP-1128, IFO14466), *Pseudogluconobacter saccharoketogenes* 12-15 (FERM BP-1132, IFO14482), *Pseudogluconobacter saccharoketogenes* 12-4 (FERM BP-1131, IFO14483) and *Pseudogluconobacter saccharoketogenes* 22-3 (FERM BP-1133, IFO14484) (Patent Document 7).

However, as is explained in detail in the subsequently described working examples, these strains have a low specificity for oxidation of the hydroxymethyl group of glucose, and form glucose oxides other than glucuronic acid, such as gluconic acid and 2-ketogluconic acid. That is, up until now, in the field of the present art, microorganisms suitable for glucuronic acid fermentation in which glucuronic acid is produced directly from glucose in the same way as in gluconic acid fermentation, and methods for producing glucuronic acid and/or glucuronolactone by glucuronic acid fermentation using such microorganisms have yet to be established.

Patent Document 1: Japanese Examined Patent Publication No. S43-5882
Patent Document 2: Japanese Laid-open Patent Publication No. H10-251263
Patent Document 3: Japanese Laid-open Patent Publication No. H11-147043
Patent Document 4: Japanese Laid-open Patent Publication No. 2006-314223
Patent Document 5: Japanese Laid-open Patent Publication No. H5-68542
Patent Document 6: Japanese Laid-open Patent Publication No. 2003-159079
Patent Document 7: Japanese Laid-open Patent Publication No. H6-7157

In light of these circumstances, the inventors have reflected on the above prior art and conducted repeated and extensive investigations with the aims of producing glucuronic acid directly from glucose in the same way as in gluconic acid fermentation as well as developing microorganisms which have a high specificity for oxidation of the hydroxymethyl group of glucose and are suitable for glucuronic acid fermentation, and of developing a new method for producing glucuronic acid and/or glucuronolactone that utilizes such microorganisms. As a result, the inventors have discovered novel mutant strains having the ability to specifically oxidize the hydroxymethyl group of glucose, and have also succeeded in establishing a new method for producing glucuronic acid and/or glucuronolactone using the mutant strains or treated forms of the cells thereof.

DISCLOSURE OF THE INVENTION

The objects of the present invention are to provide novel mutant strains having the ability to specifically oxidize the hydroxymethyl group of glucose, and to provide a novel method for producing glucuronic acid and/or glucuronolactone which includes a glucuronic acid fermentation step that uses such mutant strains and which is high-yielding, low-cost, convenient, and takes the environment into account.

The present invention for solving the above problems is constituted of the following technical means.

(1) A microorganism which produces glucuronic acid directly from glucose, characterized by that the microorganism has an ability to specifically oxidize a hydroxymethyl group of glucose, and a DNA nucleotide sequence corresponding to 16S rRNA thereof has the nucleotide sequence of SEQ ID NO: 1 in the sequence listing.

(2) The microorganism according to (1) above, wherein the DNA nucleotide sequence corresponding to 16S rRNA thereof has at least 97% homology with the nucleotide sequence of SEQ ID NO: 1.

(3) The microorganism according to (1) or (2) above, wherein the microorganism is *Pseudogluconobacter saccharoketogenes* Rh47-3, Accession No.: FERM BP-10820.

(4) A method for producing glucuronic acid and/or glucuronolactone, the method comprising: contacting the microorganism of any one according to (1) to (3) above, or a treated form thereof, with glucose in a reaction system for glucuronic acid fermentation so as to specifically oxidize the hydroxymethyl group of glucose and form glucuronic acid and/or glucuronolactone.

(5) The method according to (4) above, wherein the treated form thereof is a cell disruptate, a cell extract, or an acetone powder thereof.

(6) The method according to (4) above, wherein the glucuronic acid-forming reaction system is adjusted according to a reaction temperature in a range of between 10 and 45° C. and according to a reaction solution pH in a range of between 4 and 9.

(7) The method according to (4) above, wherein shaking or aeration and stirring is carried out in the course of glucuronic acid fermentation, and a point in time when substantially all the glucose in the reaction solution has been oxidized is treated as a reaction endpoint.

(8) The method according to (4) above, wherein the reaction solution containing the glucuronic acid that has formed is concentrated, the concentrate is inoculated with glucuronic acid metal salt crystals to effect crystallization and a metal salt of glucuronic acid is isolated and purified, or the reaction solution is desalted then concentrated, the concentration is inoculated with glucuronolactone crystals to effect crystallization, and glucuronolactone is isolated and purified.

Next, the present invention is described in greater detail.

The inventors have conducted extensive investigations in order to solve the above problems. As a result, by carrying out mutational treatment on known strains such as *Pseudogluconobacter saccharoketogenes* K591s, they have succeeded in obtaining novel mutant strains such as *Pseudogluconobacter saccharoketogenes* Rh47-3 which, compared with already existing strains, have an ability to specifically oxidize the hydroxymethyl group of glucose and a high glucuronic acid fermentative capacity. In addition, the inventors have succeeded in efficiently producing glucuronic acid at a high selectivity by bringing glucose into contact with this mutant strain.

In a first aspect, the invention is directed at a microorganism having an excellent ability to specifically oxidize the hydroxymethyl group of glucose, and more particularly to a microorganism having an ability to specifically oxidize the hydroxymethyl group of glucose, which microorganism includes DNA corresponding to 16S rRNA that has the nucleotide sequence of SEQ ID NO: 1 or includes a nucleotide sequence having at least 97% homology with the nucleotide sequence of SEQ ID NO: 1. This invention is also directed at novel mutant strains such as *Pseudogluconobacter saccharoketogenes* Rh47-3 (deposited at an official depositary institution as Accession No.: FERM BP-10820).

In a second aspect, the invention is directed at a method for producing glucuronic acid and/or glucuronolactone by glucuronic acid fermentation wherein the above mutant strain and/or a treated form of the cells thereof is contacted with glucose; that is, a method for producing glucuronic acid and/or glucuronolactone which is characterized by bringing the above microorganism or a treated form of the cells thereof into contact with glucose so as to specifically oxidize the hydroxymethyl group of glucose and form glucuronic acid.

The microorganism of the present invention is a microorganism which belongs to the genus *Pseudogluconobacter* and has DNA corresponding to 16S rRNA having at least 97% homology with the nucleotide sequence of SEQ ID NO: 1 in the sequence listing. Also, the microorganism of the invention has the microbiological characteristics shown in Table 1. In addition, compared with hitherto known microorganisms which oxidize hydroxymethyl groups, the microorganism of the invention has the ability to specifically oxidize the hydroxymethyl group of glucose and is suitable for use in glucuronic acid fermentation. In the present invention, "ability to specifically oxidize a hydroxymethyl group of glucose" refers to the ability to directly produce glucuronic acid from glucose in a ratio of from 50 to 100%, preferably from 60 to 100%, and more preferably from 70 to 100%, by oxidation of the hydroxymethyl group of glucose.

TABLE 1

Microbiological characteristics of *Pseudogluconobacter saccharoketogenes* Rh47-3

| | |
|---|---|
| Cell shape | rods (0.7-0.9 × 1.5-3.0 μm) |
| Gram staining | – |
| Motility | + |
| Presence/Absence of spores | – |
| Colony characteristics | Medium: 2.0% sorbitol, 1.0% peptone, 1.0% yeast extract, 2.0% agar |
| | Incubation time: 48 hours |
| | Diameter: 1.0-2.0 mm |
| | Color: light yellow |
| | Shape: circular |
| | Bulges: lenticular |
| | Periphery: entire margin |
| | Surface shape: smooth |
| | Transparency: opaque |
| | Consistency: butter-like |
| Incubation temperature | 37° C.: + |
| | 45° C.: + |
| Catalase reaction | + |
| Oxidase reaction | + |
| Acid/gas produced from glucose (acid produced/gas produced) | –/– |
| O/F (oxidation/fermentation) test | –/– |

TABLE 1-continued

Microbiological characteristics of *Pseudogluconobacter saccharoketogenes* Rh47-3

| | |
|---|---|
| Nitrate reduced | − |
| Indole produced | − |
| Arginine dihydrolase | − |
| Urease | − |
| Esculin hydrolyzed | + |
| Gelatin hydrolyzed | − |
| β-Galactosidase | + |
| Utilization | glucose: − |
| | L-arabinose: − |
| | D-mannose: − |
| | D-mannitol: − |
| | N-acetyl-D-glucosamine: − |
| | lactose: − |
| | maltose: − |
| | potassium gluconate: − |

The nucleotide sequence of SEQ ID NO: 1 in the sequence listing is a nucleotide sequence which codes for the 16S rRNA gene of the inventive microorganism. In a case where the DNA nucleotide sequence corresponding to 16S rRNA in a particular strain has at least 97% homology with the nucleotide sequence of a known strain, the former strain is judged to be congeneric with the known strain. Therefore, all microorganisms which have a nucleotide sequence of at least 97% homology with the nucleotide sequence of SEQ ID NO: 1 in the sequence listing and have the ability to specifically oxidize the hydroxymethyl group of glucose fall within the scope of this invention.

The microorganisms which have at least 97% homology with the nucleotide sequence of SEQ ID NO: 1 in the sequence listing are novel mutant strains created by inserting a mutation into a *Pseudogluconobacter* sp. strain. Illustrative examples include mutants created by inserting a mutation into the following parent strains: *Pseudogluconobacter saccharoketogenes* K591s, *Pseudogluconobacter saccharoketogenes* 12-5, *Pseudogluconobacter saccharoketogenes* TH14-86, *Pseudogluconobacter saccharoketogenes* 12-15, *Pseudogluconobacter saccharoketogenes* 12-4, and *Pseudogluconobacter saccharoketogenes* 22-3.

Preferred techniques for introducing mutations into *Pseudogluconobacter* sp. strains include methods of random mutation such as ultraviolet irradiation, exposure to ionizing radiation and treatment with a chemical mutagen, e.g., N-methyl-N'-nitro-N-nitrosoguanidine, and methods for introducing site-specific mutations such as by gene recombination. The *Pseudogluconobacter saccharoketogenes* Rh47-3 strain, which is a novel mutant strain the inventors created by introducing a mutation, was deposited on Apr. 4, 2007 with the International Patent Organism Depositary at Japan's National Institute of Advanced Industrial Science and Technology as FERM P-21286, and on Apr. 26, 2007 was transferred to the same international depositary authority and accessioned as FERM BP-10820.

In this invention, to determine whether a microorganism has the ability to specifically oxidize the hydroxymethyl group of glucose, use may be made of a technique for investigating the oxidation specificity of the microorganism with respect to hydroxymethyl groups of the glucose. An illustrative, non-limiting, example of such a technique is a method in which cultured cells are collected by centrifugal separation, then added to a 10% glucose solution containing 1.5% calcium carbonate and reacted under shaking for about two days, after which the proportion of glucuronic acid that has formed is verified by a high-performance chromatography (column, Shim-pack SCR101H; eluant, 20 mM sulfuric acid; column temperature, 25° C.; flow rate, 0.5 mL/min; detector, differential refractometer).

By using such a technique to determine whether a microorganism has the ability to specifically oxidize the hydroxymethyl group of glucose, it is possible to check if the DNA nucleotide sequence corresponding to the 16S rRNA of the microorganism being tested has at least 97% homology with the nucleotide sequence of SEQ ID NO: 1 in the sequence listing and to check if this microorganism has the ability to specifically oxidize the hydroxymethyl group of glucose, thus enabling one to judge whether the microorganism falls within the scope of the present invention.

The microorganisms according to the present invention may be utilized as microorganisms for glucuronic acid fermentation which produces glucuronic acid and/or glucuronolactone. The use of such microorganisms requires that a culture of the microorganism be carried out. The microorganisms of the present invention which belong to the genus *Pseudogluconobacter* may be cultured under aerobic conditions in a liquid medium containing carbon sources such as glucose, sucrose and starch; nitrogen sources such as ammonium salts, urea, corn steep liquor, yeast extract and peptone; inorganic salts of, e.g., sodium, potassium, calcium, magnesium, iron, manganese and cobalt; and, as micronutrients, vitamins and coenzymes such as CoA, pantothenic acid, biotin, thiamine and riboflavin.

The pH during culturing is typically between 4 and 9, preferably between 5 and 8, and more preferably between 6 and 7. The preferred temperature range for carrying out cultivation is typically between 10 and 45° C., preferably between 20 and 40° C., and more preferably between 25 and 35° C. The incubation time varies according to the composition of the medium, but is generally between 10 and 100 hours, and preferably between 20 and 70 hours.

The cells that have been cultured in this way are furnished for glucuronic acid fermentation. In the glucuronic acid fermentation step, live cells or a treated form of those cells act on the glucose serving as the substrate for glucuronic acid fermentation. As used herein, "a treated form of the cells" refers to a cell disruptate obtained by using a homogenizer, glass beads or the like to physically disrupt the cells, to a cell extract obtained by treating the cells with a chemical agent such as a surfactant or an enzyme, or to an acetone powder of either.

By immobilizing the cells or a treated form thereof on a carrier, these may be repeatedly used in glucuronic acid fermentation. Exemplary methods for such immobilization include methods involving adsorption onto a cellulose carrier, a ceramic carrier or a glass bead carrier; and methods that involve inclusion in calcium alginate, carrageenan or the like.

In the glucuronic acid fermentation step, the cells or treated form of the cells thereof prepared as described above are added to the glucose serving as the substrate, and reaction is effected while regulating the reaction temperature and the pH of the reaction mixture as required. The glucose concentration of the reaction mixture is generally in a range of from 1 to 30% (w/v), preferably from 3 to 20% (w/v), and most preferably from 5 to 10% (w/v).

The reaction temperature, like the culturing temperature, is generally between 10 and 45° C., preferably between 20 and 40° C., and more preferably between 25 and 35° C. The reaction pH is generally in a range of between 4 and 9, and preferably between 6 and 8. Sodium hydroxide, potassium hydroxide, calcium carbonate or the like may be added to control the pH. A means such as shaking or aeration and stirring is desirable as the reaction method. If the reaction proceeds too far, the aldehyde group on glucuronic acid will start to oxidize further. Therefore, it is preferable for the reaction time to be set in such a way that the point in time when the glucose within the reaction mixture has substantially oxidized is treated as the reaction endpoint. Example of techniques for identifying the endpoint include the above-mentioned high-performance chromatography and methods involving the use of a commercial glucose assay kit (e.g., Glucose CII Test Wako, available from Wako Pure Chemical Industries, Ltd.).

To isolate and purify the glucuronic acid metal salt from the reaction mixture obtained in this way, the reaction mixture is concentrated, then crystals of glucuronic acid metal salt are inoculated to induce crystallization, following which isolation and purification are carried out. In addition, the crystals of glucuronic acid metal salt obtained are dissolved in water, then desalted by a conventional method to give glucuronic acid. To isolate and purify glucuronolactone, the reaction mixture is desalted by a conventional method, then concentrated, following which glucuronolactone crystals are inoculated to induce crystallization, then isolated and purified.

The glucuronic acid and glucuronolactone maintain a state of equilibrium in the solution after desalting, but because the glucuronolactone more readily crystallizes, it is generally concentrated to a solid content of from 40 to 80% (w/v), at which point seed crystals of glucuronolactone are inoculated therein, following which the glucuronolactone crystals are recovered.

Alternatively, glucuronic acid and/or glucuronolactone may be isolated and purified using, for example, a method that involves adding an organic solvent to the reaction mixture, followed by precipitation and recovery of the target substance, a column separation method such as adsorption chromatography and ion-exchange chromatography, or a membrane separation method using an electrodialyzer.

Because the glucuronic acid and/or glucuronolactone obtained by the glucuronic acid fermentation method of the invention have purities which are comparable to or higher than those obtained by known methods, as with conventional products, they are useful as products having applications in a broad range of fields, including the pharmaceuticals industry, food industry and chemical products industries.

The following effects are achieved by the present invention.
(1) The present invention makes it possible to provide novel mutant strains which, compared with prior strains, have the ability to specifically and directly oxidize the hydroxymethyl group of glucose, and thus have an excellent glucuronic acid fermentative capacity.
(2) By using these mutant strains, glucuronic acid and/or glucuronolactone can be produced from glucose at a high selectivity and in a high yield.
(3) With glucuronic acid fermentation, a new method of manufacturing glucuronic acid that enables glucuronic acid to be produced directly from glucose can be provided.
(4) The method of this invention enables glucuronic acid and/or glucuronolactone to be produced at a low cost compared with conventional production methods.
(5) In the method according to the present invention, because nitrogen oxides such as nitric acid are not used, glucuronic acid and/or glucuronolactone can be produced safely and without impacting the environment.

BEST MODE FOR CARRYING OUT THE INVENTION

Next, the novel mutant strains of the invention, and the production of glucuronic acid and/or glucuronolactone using such strains are explained more concretely by way of working examples. However, it is to be understand that these examples do not limit in any way the present invention.

WORKING EXAMPLE 1

Acquisition of Mutant Strain

In the present example, an attempt was made to acquire a mutant strain by using a known strain as the parent strain. A flat-plate agar medium composed of 2.0% sorbitol, 1.0% peptone, 1.0% yeast extract and 2.0% agar was smeared with 100 μL of a suspension ($10^6$ cells/mL) of *Pseudogluconobacter saccharoketogenes* K591s, following which the cells were irradiated with ultraviolet light so that the survival ratio was 1% or less and cultured at 30° C. for 3 days.

The strain that grew was inoculated into 200 μL of a pre-culture medium composed of 1.0% lactose, 1.0% yeast extract, 0.3% ammonium sulfate, 2.0% corn steep liquor and 1.0% calcium carbonate (pH 7.0), and shake cultured at 30° C. for 1 day at 150 rpm.

Next, 800 μL of a main culture medium composed of 2.0% lactose, 0.5% yeast extract, 1.0% corn steep liquor, 0.3% ammonium sulfate, 0.1% ferrous sulfate, 0.01% lanthanum chloride and 0.5% calcium carbonate (pH 7.0) was added to the culture medium and culturing additionally carried out for 1 day, after which the cells were recovered by centrifugal separation.

The cells obtained by the above method were re-suspended in 1 mL of 10% glucose, shaken at 30° C. for 1 day, and glucuronic acid fermentation was carried out. The amount of glucuronic acid that had formed was measured by high-performance chromatography, and screened for mutant strains having a high glucuronic acid fermentative capacity (initial screening). As a result, the novel mutant strain *Pseudogluconobacter saccharoketogenes* Ps18-31 which oxidizes the hydroxymethyl group on glucose with a greatly increased specificity compared with the parent strain *Pseudogluconobacter saccharoketogenes* K591s, was acquired.

Next, the above *Pseudogluconobacter saccharoketogenes* Ps18-31 strain was inoculated into 3 mL of the above preculture medium and cultured for 1 day, following which the cells were harvested by centrifugal separation and suspended in 1 mL of a 100 mM phosphate buffer (pH 6.5). N-Methyl-N'-nitro-N-nitrosoguanidine was added to the suspension to a final concentration of 1 mg/mL, and treatment was carried out for 1 hour 30 minutes. The treated suspension was smeared onto a flat-plate agar medium and cultured at 30° C. for 3 days.

The grown strain was cultured and glucuronic acid fermentation was carried out in the same way as in the above initial screening. As a result, *Pseudogluconobacter saccharoketogenes* Rh24-6, *Pseudogluconobacter saccharoketogenes* Rh38-15, and *Pseudogluconobacter saccharoketogenes* Rh47-3 were obtained as novel mutant strains which oxidize the hydroxymethyl group on glucose with an improved specificity compared with the strain *Pseudogluconobacter saccharoketogenes* Ps18-31.

WORKING EXAMPLE 2

Glucuronic Acid Fermentation

Using the known strains and novel mutant strains shown in Table 2, glucuronic acid fermentation was carried out in accordance with the method described in Working Example 1. Fermentation was carried out until substantially all the glucose was oxidized, and the production rate of glucuronic acid based on the glucose was measured. As a result, as shown in Table 2, it was found that the novel mutant strains produced glucuronic acid from glucose in a higher yield than did the known strains.

Of these novel mutant strains, *Pseudogluconobacter saccharoketogenes* Rh47-3 produced glucuronic acid in a yield of 81.2%. This strain, *Pseudogluconobacter saccharoketogenes* Rh47-3, has been internationally deposited as Accession No. FERM BP-10820 with the International Patent Organism Depositary, an international depositary authority, at Japan's National Institute of Advanced Industrial Science and Technology. A partial nucleotide sequence of the 16S rRNA gene of this strain *Pseudogluconobacter saccharoketogenes* Rh47-3 is shown in Table 3 and as SEQ ID NO: 1 in the sequence listing.

TABLE 2

Production rate of glucuronic acid from glucose

| | Strain used | Glucuronic acid production rate (%) |
|---|---|---|
| Known strains | *Pseudogluconobacter saccharoketogenes* K591s | 6.6 |
| | *Pseudogluconobacter saccharoketogenes* 12-5s | 5.0 |
| | *Pseudogluconobacter saccharoketogenes* TH14-86 | 42.1 |
| | *Pseudogluconobacter saccharoketogenes* 12-15 | 9.6 |
| | *Pseudogluconobacter saccharoketogenes* 12-4 | 24.0 |
| | *Pseudogluconobacter saccharoketogenes* 22-3 | 40.7 |
| Novel mutant strains | *Pseudogluconobacter saccharoketogenes* Ps18-31 | 51.8 |
| | *Pseudogluconobacter saccharoketogenes* Rh24-6 | 59.4 |
| | *Pseudogluconobacter saccharoketogenes* Rh38-15 | 64.3 |
| | *Pseudogluconobacter saccharoketogenes* Rh47-3 | 81.2 |

WORKING EXAMPLE 3

Production of Sodium Glucuronate

Glucuronic acid fermentation was carried out using a 500 L fermentation tank. The tank was charged with 30 kg of glucose and 250 L of water. Following dissolution of the glucose in the water, 50 L of a washed suspension of *Pseudogluconobacter saccharoketogenes* Rh47-3 cells that had been separately cultured using the medium described in Working Example 1 was added to the solution, and fermentation was carried out under aeration with air at a rate of 100 L/min. The stirring rate was 200 rpm, the temperature was 30° C., and the pH was adjusted to 6.0 using a 12% (w/v) sodium hydroxide solution. When the amount of glucose remaining had fallen below 0.5% (w/v), fermentation was stopped by 30 minutes of heating at 90° C.

Fermentation converted about 80% of the glucose into sodium glucuronate; the time required to do so was 42 hours. Next, filtration using an ultrafiltration (UF) membrane was carried out and the ultrafiltrate was recovered and concentrated to 60% (w/v), following which 300 g of seed crystals of sodium glucuronate was added, followed by cooling to 20° C. The crystals that settled out were centrifugally separated, giving 15.6 kg of crude sodium glucuronate. This crude product was re-crystallized, yielding 12.2 kg of refined sodium glucuronate having a purity of at least 99.9%.

WORKING EXAMPLE 4

Preparation of Glucuronolactone

Sodium glucuronate was prepared from 30 kg of glucose in accordance with the method described in Working Example 3, and ultrafiltrate was recovered from filtration with an ultrafiltration (UF) membrane. The resulting ultrafiltrate was desalted by being passed through 50 L of a strongly acidic ion-exchange resin (Diaion PK-216, available from Mitsubishi Chemical Corporation). The desalted liquid was concentrated to 72% (w/v), after which the equilibrium ratio of glucuronic acid and glucuronolactone within the solution was moved so as to increase the glucuronolactone content, then 300 g of seed crystals of glucuronolactone was added and cooling was carried out to 20° C., inducing crystallization of the glucuronolactone. The crystals were recovered by centrifugal separation, giving 10.1 kg of crude glucuronolactone. This crude product was re-crystallized, yielding 8.4 kg of refined glucuronolactone having a purity of at least 99.9%.

TABLE 3

GAGTTTGATCCTGGCTCAGAACGAACGCTGGCGGCAGGCTTAACACATGC

AAGTCGAACGCCCCGCAAGGGGAGTGGCAGACGGGTGAGTAACGCGTGGG

AATCTACCCAGTTCTTCGGAATAACWSAGGGAAACTTSWGCTAATACCGG

ATACGCCCTACGGGGAAAGATTTATCGGAATTGGATGAGCCCGCGTAAG

ATAGCTAGTTGGTGAGGTAACGGCTCACCAAGGCGACGATCTTTAGCTGG

TCTGAGAGGATGATCAGCCACACTGGGACTGAGACACGGCCCAGACTCCT

ACGGGAGGCAGCAGTGGGGAATATTGGACAATGGGCGCAAGCCTGATCCA

GCCATGCCGCGTGAGTGATGAAGGCCTTAGGGTTGTAAAGCTCTTTCAGT

AGGGAAGATAATGACGGTACCTACAGAAGAAGCCCCGGCTAACTTCGTGC

CAGCAGCCGCGGTAATACGAAGGGGGCTAGCGTTGTTCGGATTTAGTGGG

CGTAAAGCGCACGTAGGCGGATTGTTAAGTTAGGGGTGAAATCCCAGGGC

TCAACCCTGGAACTGCCTTTAATACTGGCAATCTAGAGTCCGGAAGAGGT

GAGTGGAACTCCTAGTGTAGAGGTGGAATTCGTAGATATTAGGAAGAACA

CCAGTGGCGAAGGCGGCTCACTGGTCCGGTACTGACGCTGAGGTGCGAAA

GCGTGGGGAGCAAACAGGATTAGATACCCTGGTAGTCCACGCCGTAAACT

ATGAGAGCTAGCCGTTGGGAWGTTTACWTCTCAGTGGCGCAGCTAACGCA

TTAAGCTCTCCGCCTGGGGAGTACGGTCGCAAGATTAAAACTCAAAGGAA

TTGACGGGGGCCCGCAGAAGCGGTGGAGCATGTGGTTTAATTCGAAGCAA

CGCGAAGAACCTTACCAGCCCTTGACATCCCGGTCGCGGTTTTCAGAGAT

GAATTCCTTCAGTTCGGCTGGACCGGTGACAGGTGCTGCATGGCTGTCGT

CAGCTGGTGTCGTGAGATGTTGGGTTAAGTCCCGCAACGAGCGCAACCCT

GGCCTTTAGTTGCCATCATTTAGTTGGGCACTCTAGAGGGACTGCCGGTG

ATAAGCCGGAGGAAGGTGGGGATGACGTCAAGTCATCATGGCCCTTACGG

GCTGGGCTACACAGGTGCTACAATGGCGGTGACAGAGGGCAGCTACACGG

CGACGTGATGCTAATCCCTAAAAACCGTCTCAGTTCGGATTGCACTCTGC

AACTCGGGTGCATGAAGTTGGAATCGCTAGTAATCGCAGATCAGCATGCT

TABLE 3-continued

```
GCGGTGAATACGTTCCCGGGCCTTGTACACACCGCCCGTCACACCATGGG
AGTTGGTTCTACCCGAAGCCGGTGCGCTAACCGCAAGGAAGCAGCCGACC
ACGGTAGGGTCAGCGACTGGGGTGAAGTCGTAAGAAGGTAGCC
```

INDUSTRIAL APPLICABILITY

As described in detail above, the present invention relates to a method for producing glucuronic acid by glucuronic acid fermentation. By means of this invention, there can be provided novel mutant strains which have the ability to specifically and directly oxidize the hydroxyl group of glucose and are thus highly suitable for the production of glucuronic acid and/or glucuronolactone, and also methods for producing glucuronic acid and/or glucuronolactone using such mutant strains. The novel mutant strains of *Pseudogluconobacter saccharoketogenes* of the present invention have capabilities suitable for glucuronic acid fermentation. Hence, by using these microorganisms, glucuronic acid and/or glucuronolactone can be easily and safely produced from glucose in a high yield and at a lost cost. The present invention is useful for providing a new glucuronic acid production method that makes it possible to produce glucuronic acid directly from glucose.

Concerning Deposition of the Microorganisms
Name of International Depositary Authority:
  International of patent organism depositary at national Institute of advanced industrial science and technology
Address: Chuo 6, 1-1-1
  Tsukuba-shi, Ibaraki 305-80566
  Japan
Date of Acceptance: Apr. 26, 2007
Accession No.: Ferm BP-10820
Designation of Microorganism: Rh47-3

The invention claimed is:

1. A biologically pure microorganism of *Pseudoglucono-bacter saccaroketogenes* FERM BP-10820 which produces glucuronic acid directly from glucose, wherein the microorganism has an ability to specifically oxidize a hydroxymethyl group of glucose, and contains the DNA nucleotide sequence encoding the nucleotide sequence of the 16s rRNA as set forth in SEQ ID NO: 1.

2. A method for producing glucuronic acid and/or glucuronolactone, the method comprising:
   contacting the microorganism of claim 1 with glucose in a reaction system for glucuronic acid fermentation whereby the hydroxymethyl group of glucose is specifically oxidized to form glucuronic acid and/or glucuronolactone.

3. The method according to claim 2, wherein said microorganism is in the form of an acetone powder.

4. The method according to claim 2, wherein the glucuronic acid-forming reaction system is adjusted to a reaction temperature in a range of between 10 and 45° C. and to a reaction solution pH in a range of between 4 and 9.

5. The method according to claim 2, wherein shaking or aeration and stirring is carried out in the course of glucuronic acid fermentation, and wherein the point in time when substantially all the glucose in the reaction solution has been oxidized is treated as a reaction endpoint.

6. The method according to claim 2, wherein
   (i) a reaction solution containing the glucuronic acid that has formed is concentrated, the concentrate is inoculated with glucuronic acid metal salt crystals to effect crystallization and a metal salt of glucuronic acid is isolated and purified, or
   (ii) the said reaction solution is desalted and then concentrated, the concentrate is inoculated with glucuronolactone crystals to effect crystallization, and glucuronolactone is isolated and purified.

* * * * *

SEQUENCE LISTING

<160> NUMBER OF SEQ ID NOS: 1

<210> SEQ ID NO 1
<211> LENGTH: 1444
<212> TYPE: DNA
<213> ORGANISM: Pseudogluconobacter

<400> SEQUENCE: 1

```
gagtttgatc ctggctcaga acgaacgctg gcggcaggct taacacatgc aagtcgaacg      60
ccccgcaagg ggagtggcag acgggtgagt aacgcgtggg aatctaccca gttcttcgga     120
ataacwsagg gaaacttswg ctaataccgg atacgcccta cggggaaag atttatcgga      180 attggatgag cccgcgtaag attagctagt tggtgaggta acggctcacc aaggcgacga     240
tctttagctg gtctgagagg atgatcagcc acactgggac tgagacacgg cccagactcc     300
tacgggaggc agcagtgggg aatattggac aatgggcgca agcctgatcc agccatgccg     360
cgtgagtgat gaaggcctta gggttgtaaa gctctttcag tagggaagat aatgacggta     420
cctacagaag aagcccggc taacttcgtg ccagcagccg cggtaatacg aaggggcta       480 gcgttgttcg gatttactgg gcgtaaagcg cacgtaggcg gattgttaag ttagggtga      540 aatcccaggg ctcaaccctg gaactgcctt taatactggc aatctagagt ccggaagagg     600
tgagtggaac tcctagtgta gaggtggaat tcgtagatat taggaagaac accagtggcg     660
aaggcggctc actggtccgg tactgacgct gaggtgcgaa agcgtgggga gcaaacagga     720
ttagataccc tggtagtcca cgccgtaaac tatgagagct agccgttggg awgtttacwt     780
ctcagtggcg cagctaacgc attaagctct ccgcctgggg agtacggtcg caagattaaa     840
actcaaagga attgacgggg gcccgcacaa gcggtggagc atgtggttta attcgaagca     900
acgcgaagaa ccttaccagc ccttgacatc ccggtcgcgg ttttcagaga tgaattcctt     960
cagttcggct ggaccggtga caggtgctgc atggctgtcg tcagctcgtg tcgtgagatg    1020
ttgggttaag tcccgcaacg agcgcaaccc tcgccttag ttgccatcat ttagttgggc     1080
actctagagg gactgccggt gataagccgg aggaaggtgg ggatgacgtc aagtcatcat    1140
ggcccttacg ggctgggcta cacacgtgct acaatggcgg tgacagaggg cagctacacg    1200
gcgacgtgat gctaatccct aaaaccgtc tcagttcgga ttgcactctg caactcgggt     1260
gcatgaagtt ggaatcgcta gtaatcgcag atcagcatgc tgcggtgaat acgttcccgg    1320
```

```
gccttgtaca caccgcccgt cacaccatgg gagttggttc tacccgaagc cggtgcgcta    1380
accgcaagga agcagccgac cacggtaggg tcagcgactg gggtgaagtc gtaacaaggt    1440
agcc                                                                 1444
```